United States Patent [19]

Pesa et al.

[11] Patent Number: 4,551,442

[45] Date of Patent: Nov. 5, 1985

[54] CATALYST FOR UPGRADING SYNTHESIS GAS

[75] Inventors: Frederick A. Pesa, Aurora; Anne M. Graham, Northfield, both of Ohio

[73] Assignee: The Standard Oil Company (Ohio), Cleveland, Ohio

[21] Appl. No.: 653,395

[22] Filed: Sep. 24, 1984

Related U.S. Application Data

[60] Division of Ser. No. 557,725, Dec. 2, 1983, Pat. No. 4,496,666, which is a continuation of Ser. No. 333,218, Dec. 21, 1981, abandoned.

[51] Int. Cl.$^4$ ................. B01J 21/04; B01J 21/08; B01J 23/78
[52] U.S. Cl. ................. 502/178; 502/243; 502/330
[58] Field of Search ............ 502/178, 243, 330, 333, 502/334; 423/593

[56] References Cited

U.S. PATENT DOCUMENTS

| | | | |
|---|---|---|---|
| 2,535,060 | 12/1950 | Gresham | 518/718 |
| 2,549,470 | 4/1951 | Howk et al. | 502/170 X |
| 4,086,262 | 4/1978 | Chang et al. | 518/716 |
| 4,199,522 | 4/1980 | Murchison et al. | 502/220 X |

*Primary Examiner*—W. J. Shine
*Attorney, Agent, or Firm*—T. P. Schur; J. G. Curatolo; L. W. Evans

[57] ABSTRACT

Catalysts comprising the mixed oxides of ruthenium, palladium or platinum and alkali metals are provided which are useful in the subject process for the upgrading of synthesis gas, particularly for obtaining alkanes and alcohols having at least two carbon atoms, in addition to methane and methanol. Also provided is a temperature gradient reactor useful in synthesis gas upgrading reactions for increasing selectivity to higher carbon number products.

8 Claims, No Drawings

CATALYST FOR UPGRADING SYNTHESIS GAS

This is a division of application Ser. No. 557,725 filed Dec. 2, 1983, now U.S. Pat. No. 4,496,666, which is a continuation of application Ser. No. 333,218, filed Dec. 21, 1981, now abandoned.

TECHNICAL FIELD

The present invention is directed to the upgrading of synthesis gas to produce mixtures of hydrocarbons.

More particularly, the present invention is directed to a vapor phase reaction of synthesis gas comprising carbon monoxide and hydrogen in the presence of a catalyst to produce mixtures of hydrocarbons and oxygenated hydrocarbons, wherein alkane and alcohol products predominate, including higher alcohols.

The present invention is further directed to the upgrading of synthesis gas to optimize production of higher alcohols by utilizing a heat gradient reactor.

BACKGROUND OF THE INVENTION

U.S. Pat. Nos. 2,535,060 to Gresham and 2,549,470 to Howk et al. disclose the preparation of straight-chain primary hydroxyalkanes by introducing hydrogen, carbon monoxide and a hydroxylated solvent into a reaction vessel and heating the mixture in the presence of a ruthenium-containing catalyst (particularly ruthenium metal, oxide, carbonyl, or salts of carboxylic acids which give rise to formation of the carbonyl) and in Howk et al., in the presence of an alkaline reagent by maintaining pH in the range of 7.0 to 11.5. Both Gresham and Howk et al. teach that it is essential that the reaction take place in the liquid phase.

U.S. Pat. No. 3,941,819 to Vannice et al. describes the production of ethane, ethylene and dimethyl ether by passing a carbon monoxide and hydrogen mixture over platinum supported on alumina.

U.S. Pat. No. 4,086,262 to Chang et al. describes the production of hydrocarbon mixtures by contacting a mixture of carbon monoxide and hydrogen with a carbon monoxide reduction catalyst and an acidic crystalline alumino silicate (zeolite). Chang et al. teach that prominent types of catalysts include metals or oxides of Zn, Fe, Co, Ni, Ru, Th, Rh, and Os, and that "with the exception of ruthenium, all practical art recognized synthesis catalysts contain chemical and structural promotors".

U.S. Pat. No. 4,119,656 describes the production of one to 2 carbon atom oxygenated hydrocarbons by contacting synthesis gas with a catalyst consisting essentially of palladium.

U.S. Pat. No. 4,171,320 to Vannice discloses the selective production of olefins from carbon monoxide and hydrogen using as a catalyst, ruthenium on a support comprising at least one refractory Group VB metal oxide.

U.S. Pat. No. 4,199,522 to Murchison et al. discloses the preparation of olefins of 2 to 4 carbon atoms from carbon monoxide and hydrogen using catalysts comprising a sulfide, oxide or metal of Mo, W, Re, Ru, Ni, Pd, Rh, Os, Ir or Pt and a hydroxide, oxide or salt of Li, Na, K, Rb, Cs, Mg, Ca, Sr, Ba or Th.

U.S. Pat. No. 4,201,597 to Huang et al. discloses the preparation of oxygenated hydrocarbons by reacting carbon monoxide and hydrogen in the presence of a catalyst containing rhodium, tungsten and an alkali metal.

U.S. Pat. No. 4,206,134 to Kugler et al. discloses the selective preparation of low weight olefins from carbon monoxide and hydrogen using as a catalyst, ruthenium on a support consisting of a manganese-containing oxide.

U.S. Pat. No. 4,246,186 to Bhasin et al. discloses the preparation of two carbon atom oxygenated hydrocarbons from hydrogen and carbon monoxide by reaction with a rhodium metal catalyst, as compared to other single element Group VIII metal and copper catalysts.

U.S. Pat. No. 4,125,553 to Cropley discloses the production of oxygenated two carbon atom compounds from synthesis gas utilizing a rhodium catalyst, while controlling the exothermic reaction conditions to avoid production of methane, which phenomenon is otherwise taught to be caused by an increase in temperature over the length of catalyst bed.

In the past, it has been taught that it is desirable to employ gradientless reactors for chemical synthesis reactions. The prior art is replete with reports of attempts to control exotherm or hot spots in reactors, and to provide uniform operating temperatures over the length of a reactor catalyst bed.

SUMMARY OF THE INVENTION

We have found that in the upgrading of synthesis gas to hydrocarbons, including oxygenated hydrocarbons such as alcohols, it is possible to form higher alcohols having from two to nine carbon atoms by utilizing a heat gradient, vapor phase reactor, in which the temperature of the catalyst bed in the reactor increases as the reactant stream proceeds through the catalyst bed.

Independent of whether a heat gradient reactor or a gradientless reactor is utilized, we have found that catalysts comprising the mixed metal oxides of ruthenium, at least one alkali metal, and palladium or platinum are useful for the upgrading of synthesis gas to hydrocarbons, exhibiting good selectivity to alkanes and oxygenated hydrocarbon products, particularly alcohols.

It is therefore an object of the present invention to provide a process to upgrade synthesis gas to produce hydrocarbons, particularly alkanes and oxygenated hydrocarbons and more particularly alcohols, with high selectivity.

It is a further object of the present invention to provide a process to upgrade synthesis gas to produce higher alcohols having from two to about nine carbon atoms.

It is a further object of the present invention to provide novel catalyst compositions useful in the upgrading of synthesis gas to produce alkanes and oxygenated hydrocarbons, particularly alcohols.

In general, the process of the present invention includes the upgrading of synthesis gas to obtain predominantly alkanes and alcohols comprising contacting carbon monoxide and hydrogen in the vapor phase at a reaction temperature of at least 250° C. and a reaction pressure of at least 500 psi with a catalyst of the formula

$$A_a Ru M_b O_x$$

wherein
 A is an alkali metal,
 M is Pd, Pt or mixtures thereof, and
wherein
 a is about 0.002 to about 2,
 b is about 0.1 to about 10, and x is the number of oxygens needed to fulfill the valence requirements of the other elements.

The present invention further includes novel catalysts of the composition

wherein
A is an alkali metal,
M is Pd, Pt or mixtures thereof, and
wherein
a is about 0.002 to about 2,
b is about 0.1 to about 10, and
x is the number of oxygens needed to fulfill the valence requirements of the other elements.

The process of the present invention further includes a process for the upgrading of synthesis gas wherein carbon monoxide and hydrogen are contacted with a carbon monoxide hydrogenation catalyst in the vapor phase at a reaction temperature of at least 250° C. and a reaction pressure of at least 500 psi, said catalyst being contained in a catalyst bed disposed within a fixed bed reactor, said catalyst bed having a first portion through which reactant gases enter the catalyst bed and at least partially react before passing to a second portion of the catalyst bed located upstream of said first portion, in which second portion reaction continues and is completed prior to the product exiting the catalyst bed and reactor, thereby increasing product selectivity to gaseous alkanes having more than one carbon atom and to alcohols having more than two carbon atoms by maintaining a temperature gradient across the catalyst bed such that temperature of the first portion of the catalyst bed is maintained at least 30° C. lower than the temperature of the second portion.

DETAILED DESCRIPTION OF THE INVENTION

In the process of the present invention, synthesis gas, or a mixture of carbon monoxide and hydrogen is reacted in the presence of a carbon monoxide hydrogenation catalyst in the vapor phase to form hydrocarbons, and in particular, alkanes and alcohols.

Synthesis gas may be produced by means known in the art and practiced commercially, including providing synthesis gas as a product of the partial combustion of coal, natural gas, petroleum bottoms or other carbonaceous materials. One method of derivation is the heating of coke in the presence of air and then steam. The ratio of carbon monoxide to hydrogen in the synthesis gas mixture to be upgraded may vary from about 0.1:1 to 10:1 and is preferably in the range of about 1:3 to about 3:1. The synthesis gas may contain a very low amount of sulfur compounds, and may also contain small amounts of carbon dioxide, nitrogen and other inerts.

Although synthesis gas is a preferred reactant, any other gas composed primarily of hydrogen and carbon monoxide and having CO:H$_2$ ratio of 0:1:1 to 10:1 may be employed. Preferably the gaseous reactant is essentially sulfur free.

PROCESS CONDITIONS

The process of the present invention is carried out by contacting the gaseous reactants, containing carbon monoxide and hydrogen, with the novel catalyst described below in a suitable fluid bed or fixed bed reactor. The reaction can be conducted continuously or in a batch-type operation. The reaction temperature should be maintained between about 250° C. to about 400° C., preferably about 275° C. to about 375° C.

The reaction pressure should normally be maintained between about 500 psi to about 5,000 psi, preferably 500 psi to about 1500 psi. The reactant gases may be fed to the reactor utilized with a space velocity (liters gaseous reactants fed per liters of catalyst per hour) of about 100 per hour to about 10,000 per hour, preferably about 500 per hour to about 5,000 per hour.

The contact time of the reactants with the catalyst is generally between about 10 seconds to about 200 seconds, and is preferably between about 40 seconds to about 140 seconds.

CATALYST

The novel catalysts provided by the present invention are believed to be oxide complexes and comprise the composition described by the empirical formula

wherein
A is an alkali metal,
M is Pd, Pt or mixtures thereof, and
wherein
a is about 0.002 to about 2,
b is about 0.1 to about 10, and
x is the number of oxygens needed to fulfill the valence requirements of the other elements.
M is preferably palladium, and A may be selected from Na, Li, K, Rb and Cs, although Na, K and Rb are preferred.

The ratio of ruthenium to platinum or palladium is perferably about 0.5:1 to about 2:1. The presence of an alkali metal component is required in the inventive catalyst. Mixed oxide catalysts of ruthenium and palladium or ruthenium and platinum which are alkali free produce essentially all methanol as the alcohol product, with no alcohols having more than two carbon atoms being produced. The alkali metal may be present in the catalyst at a level of about 0.002 to about 2 moles alkali metal oxide per mole of ruthenium oxide. Catalysts of the above formula are preferred in which a equals about 0.02 to about 1.

The catalyst of the present invention is a mixed metal oxide. In the process of the present invention, the catalyst is preferably utilized in a partially reduced state. However, the catalyst is not totally reduced to the elemental state and thus retains its oxide character.

The catalyst may be prepared by conventional means, such as mixing compounds containing the catalyst components in a liquid solution or slurry, such as a water solution or slurry and heating; recovering the catalyst precursor from the liquid, drying and calcining. Catalyst containing compounds may include but are not limited to oxides, hydroxides, inorganic salts such as nitrates, phosphates, halides, carbonates, silicates, aluminates, and salts of organic acids such as acetates, formates, butyrates, propionates, benzylates, and the like. Preferred catalysts of the present invention, containing the alkali metal component are prepared by recovering the catalyst precursor by adding to the aqueous solution of ruthenium and platinum or palladium components, an alkali metal hydroxide to cause precipitation of the catalyst precursor, heating in the presence of the alkali metal, and thereafter filtering the precipitate.

The catalyst may be formed in a conventional manner, such as tabletting, pelleting, or supporting the active catalyst material on a carrier. The carrier is preferably inert, and may include silica, alumina, Alundum, alumina-silica, silicon carbide, clay and the like. The active catalytic material may be coated on the carrier by the method described in U.S. Pat. No. 4,077,912 or may be impregnated on the carrier such as by depositing a solution of the catalyst component containing compounds onto a carrier, drying and calcining.

HEAT GRADIENT REACTOR

We have found that selectivity to gaseous alkanes having more than one carbon atom and alcohols having more than two carbon atoms is increased when the synthesis gas upgrading reaction is carried out in a reactor having a catalyst bed divided into at least two portions, in which the temperature of the catalyst bed varies from a low temperature in the first portion of the catalyst bed where reactants first contact the catalyst, to a higher temperature in the second portion of the catalyst bed located downstream of the first portion, in which second portion the synthesis gas upgrading reaction continues and is completed prior to the product exiting the catalyst bed. This heat gradient does not correspond to the normal "hot spot" where substantial reactions occurs and the temperature of the bed then drops downstream of the flow of the reactant gases. Rather, the first portion of the catalyst bed refers to a portion in which reaction takes place but in which temperature is controlled by reactor temperature control means known in the art to remain on an average, across the area of the first portion of the bed, about 30° C. lower in temperature than the downstream second portion of the catalyst bed, as determined by the average temperature over the area of the second portion.

It is envisioned within the scope of this invention, that there be one or more intermediate portions of the catalyst bed disposed between the first and second portions, in which the temperature becomes succeedingly greater downstream of the first portion. We have found that the carbon number of the synthesis gas upgrading product produced in a reactor of this type increases as compared to such production in a gradientless reactor. The mechanism by which this phenomenon occurs is not clear. However, it is possible that lower number hydrocarbons which are formed in the low temperature region subsequently react with the synthesis gas reactants in the high temperature region to form elongation of the carbon chain.

Temperature gradient heating may be accomplished by varying the temperature along the length of the reactor catalyst bed by known reactor heating means, such as heating coils or by surrounding the reactor with a plurality of high temperature salt baths of progressively higher temperature corresponding to the direction of flow of the reactants through the reactor. Examples of known means to control reactor temperature are described in U.S. Pat. No. 4,125,553, incorporated by reference herein.

PRODUCTS

Products of the synthesis gas upgrading process of the present invention include methane, methanol, ethanol, gaseous alkanes having more than one carbon atom and alcohols having more than two carbon atoms. The alcohol products have a carbon number of one to nine, that is, there are from one to nine carbon atoms included in the alcohol products. Greater selectivity to alcohols having more than two carbon atoms is exhibited due to the inclusion of alkali metal in the catalyst, as is demonstrated by comparative examples below in which an alkali metal was excluded, resulting in predominantly methane production. Selectivity to higher alcohols is optimized when a temperature gradient reactor as described above is utilized. Trace amounts of aldehydes are present in the products of the inventive process, and little or no olefins are generally present. The alkane and alcohol products are generally linear, and include but are not limited to methane, ethane, propane, butane, methanol, ethanol, propanol, butanol, pentanol, hexanol, heptanol, octanol and nonanol. These products are useful as fuels such as gasoline additives and are suitable for use as chemical feedstocks. Where conversion is maintained at a moderate or low level, these products can be recovered from the reactor effluent, and the remaining synthesis gas recycled to the reaction.

It is expected that other catalyst systems selective for the production of other hydrocarbon products from synthesis gas would be used while utilizing the temperature gradient reactor of the present invention, and that the selectivity to high carbon number products would be optimized accordingly; therefore, such are included in the scope of the present invention.

SPECIFIC EMBODIMENTS

Catalyst Preparation

In the examples below, catalysts were prepared by the following method. An amount of ruthenium chloride and palladium acetate required to give 0.03 moles of each metal were dissolved in 250 milliliters of water with stirring for 30 minutes. Aqueous sodium hydroxide (50% by weight) was added dropwise with stirring, until the pH reached and remained at 8.3 to 8.5 (approximately 7 to 15 milliliters). The resulting slurry was heated near boiling for 30 minutes with constant stirring, then cooled. The pH was adjusted, if necessary, to 7.5. The mixture was filtered, washed, and reslurried with subsequent filtering and washing steps until the molar ratio of sodium to ruthenium present was approximately 0.02:1 to 0.2:1. The solid mixed oxide was dried at 125° C. for about 16 hours, was calcined for three hours at about 350° C. (in air) and was ground to pass 140 mesh (0.105 millimeters).

The catalysts were coated upon alumina-silica supports in the following manner. 25 grams of Norton SA 5223 Alundum, 10/30 mesh (0.595 millimeters–2.00 millimeters), were placed in a vessel. 1.25 grams distilled water was sprayed onto the Alundum which was rolled for approximately 10 minutes and the procedure was repeated. The metal oxide catalysts, in an amount calculated to give a total of 0.015 moles of active metal, was added in two equal portions with 15 minutes rolling after each. The coated catalysts were dried for about 16 hours at 125° C. and calcined three hours at 350° C. The catalyst components may be added to the supports individually in any order, if desired.

Catalyst prepared in this manner contained approximately 5 weight percent active metals (oxides), 0.01% to 0.1% by weight sodium and have surface areas of about 2 m$^2$/g, with pore volumes of from about 0.06 to about 0.09 cc/g. The catalyst in some examples as described below were prepared to contain twice the active phase loading, that is 10 weight percent active metals, and are identified accordingly herein.

The catalysts were partially reduced in the following manner. A stainless steel tube reactor was packed with catalyst, and hydrogen gas was introduced into the reactor at 150-200 cc/min. at atmospheric pressure. The electric block furnace placed around the reactor was increased in 50° increments stepwise until 500° C. was reached. The final temperature was maintained for two hours, at which time the reactor was allowed to cool with hydrogen flow being continued.

Reaction Procedure

Following catalyst reduction and subsequent cooling to room temperature, the reactor utilized was charged to the desired pressure with hydrogen. The split block electric furnaces surrounding the reactors were activated and set for run temperature. The system was allowed to equilibrate for at least 15 minutes at run temperature before carbon monoxide flow was started and both gases were adjusted to the desired flow rates. After about one to one and one-half hours of reaction, the off-gas (effluent) was sampled and analyzed and the condensible product diverted from a pre-run receiver to a product collection receiver. A recovery run proceeded for one to three hours during which time the off-gas was analyzed by gas chromatography and its volume measured. The liquid product also was weighed and analyzed.

In addition to gas chromatography analysis for the gas phase, hydrocarbons having more than three carbon atoms were determined by flame ionization detection. Liquid phase hydrocarbons and oxygenated hydrocarbons were analyzed by gas chromatography. The results reported in the Tables below were calculated as follows.

Selectivity =

$$\frac{\text{Moles Product} \times \text{number carbon atoms in product}}{\text{Moles CO input} - \text{Moles CO effluent}} \times 100$$

CO Conversion =

$$\frac{\text{Moles of CO input} - \text{moles CO effluent} \times 100}{\text{Moles of CO input}}$$

EXAMPLES

Examples 1-2

Catalysts of the formula 5% $RuPdNa_{0.02-0.2}O_x/95\%$ Alundum were prepared according to the above procedure. These catalysts were tested for synthesis gas upgrading under the reaction conditions set forth in Table I, being charged to a 40 cc temperature gradient reactor, in which the temperature range varied by 40° C. Results of the test are reported in Tables I and II.

TABLE II

| | Alcohol Distribution Using Temperature Gradient Reactor | | | | |
|---|---|---|---|---|---|
| | | % Selectivity | | | |
| Example No. | Total Alcohol | Alcohol $C_1$ | $C_2$ | $C_3$ | $>C_3$ |
| 1 | 7.1 | 3.6 | 2.1 | 1.1 | 0.2 |
| 2 | 73.0 | 43.8 | 11.9 | 11.9 | 5.4 |
| Comp. C | 10.0 | 4.7 | 3.5 | 1.8 | 0 |
| Comp. D | 24.4 | 18.6 | 3.1 | 2.6 | 0.1 |

COMPARATIVE EXAMPLES A & B

Catalysts of the formula 5% $RuO_x/95\%$ Alundum were prepared according to the above method and tested for the upgrading of synthesis gas. At temperatures of 200°-300° C. (Example A) the products obtained were predominantly methane, with some ethane and propane. When tested over 300° C. (Example B) the products obtained were high carbon number paraffinic hydrocarbons.

COMPARATIVE EXAMPLES C & D

Catalysts of the formula 5% $PdO_x/95\%$ Alundum were prepared according to the above procedure and tested for the upgrading of synthesis gas under the conditions set forth in Table I. Results of the tests are reported in Tables I and II. The palladium catalyst not containing ruthenium is generally less favorable for alcohol production and is less favorable for selectivity to higher alcohols. For example, the selectivity ratio for alcohols having more than one carbon atom as compared to the selectivities for methanol in Example 2 is 0.67, whereas in Comparative Example B the ratio is only 0.31. It is thus demonstrated that the catalysts of the present invention exhibit greater selectivity to the higher alcohols, than do the same non-combined metal oxides.

EXAMPLES 3-4

Catalysts of the formula 5% $RuPdNa_{0.02-0.2}O_x/95\%$ Alundum were prepared according to the method described above, except that rather than coating the carrier material, the carrier was impregnated with a slurry of the catalyst components. The catalysts prepared in Examples 3 and 4 as well as the catalyst compared in Comparative Examples E and F, and Examples 5-10 below were tested for synthesis gas upgrading in the 40 cc temperature gradient reactor at a $CO/H_2$ ratio of 3/7, a reaction pressure of about 1,300 psi, and a space velocity of 3,300/hr. Temperature ranges for these examples are reported in Table III below, together with the results of the tests.

TABLE I

| UPGRADING OF SYNTHESIS GAS USING TEMPERATURE GRADIENT REACTOR | | | | | | | | |
|---|---|---|---|---|---|---|---|---|
| | | | | | | % Selectivity | | |
| Example No. | Gradient Reactor Temp. Range (°C.) | Pressure (PSI) | $CO:H_2$ Ratio | Space Velocity ($hr^{-1}$) | % CO Conversion | $CH_4$ | Alkanes (gas) ($\geq C_2$) | Olefins (gas) | Alcohols |
| 1 | 335-375 | 600 | 1:1 | 510 | 5.0 | 16.1 | 13.4 | 18.7 | 7.1 |
| 2 | 310-350 | 1300 | 3:7 | 3300 | 3.3 | — | — | — | 73.0 |
| C | 335-375 | 600 | 1:1 | 510 | 11.6 | 10.5 | 4.8 | 4.6 | 10.0 |
| D | 310-350 | 1300 | 3:7 | 3300 | 0.8 | 32.0 | — | — | 24.4 |

TABLE III

UPGRADING OF SYNTHESIS GAS USING MIXED OXIDES OF RUTHENIUM, PALLADIUM AND ALKALI METAL CATALYSTS
($CO:H_2$ = 3:7, REACTION PRESSURE = 1300 PSI, SPACE VELOCITY = 3300 $hr^{-1}$, TEMPERATURE GRADIENT REACTOR)

| Example No. | Gradient Reactor Temp. Range (°C.) | % CO Conversion | % Selectivity[d] | | | | | |
|---|---|---|---|---|---|---|---|---|
| | | | Alkanes (gas) | | Alcohols | | | |
| | | | $CH_4$ | $\geq C_2$ | Total | $C_1$ | $C_2$ | $>C_2$ |
| 3 | 310–350 | 2.8 | 19.4 | — | 23.3 | 22.2 | 1.1 | trace |
| 4 | 347–387 | 1.9 | 2.9 | —[c] | 40.0 | 33.3 | 5.2 | 1.5 |
| E[a] | 310–350 | 1.3 | 42.6 | 13.1 | 29.5 | 29.5 | — | — |
| F[a] | 340–380 | 4.9 | 35.7 | 13.6 | 33.6 | 32.9 | 0.7 | — |
| 5[b] | 310–350 | 3.5 | 51.4 | 12.5 | 29.2 | 27.8 | 1.4 | — |
| 6[b] | 340–380 | 7.3 | 50.2 | 19.3 | 20.5 | 19.3 | 0.8 | 0.4 |
| 7 | 310–350 | 6.5 | 38.9 | 19.1 | 29.1 | 23.7 | 3.1 | 2.3 |
| 8 | 325–365 | 8.8 | 46.1 | 2.6 | 26.1 | 23.0 | 2.1 | 1.0 |
| 9 | 340–380 | 8.1 | 29.9 | 6.8 | 41.0 | 35.9 | 3.8 | 1.3 |
| 10 | 340–380 | 7.2 | 44.0 | 5.1 | 22.2 | 20.1 | 2.1 | trace |

[a] Alkali Metal Free
[b] Impregnated
[c] Olefins Present
[d] Trace aldehydes present except in comparative examples.

COMPARATIVE EXAMPLES E AND F space velocity as well as results of the tests are listed in Table IV below.

TABLE IV

UPGRADING OF SYNTHESIS GAS USING MIXED OXIDES OF RUTHENIUM, PALLADIUM AND ALKALI METAL CATALYSTS
($CO:H_2$ = 3:7, REACTION PRESSURE = 1300 PSI, CATALYST = ~10% W/W ACTIVE ON ALUNDUM: ~0.015 moles/2.5 gr support)

| Example No. | Temperature °C. | Space Velocity ($hr^{-1}$) | % CO Conversion | % Selectivity | | | | Alcohol Selectivity Distribution | | |
|---|---|---|---|---|---|---|---|---|---|---|
| | | | | Alkanes (gas) | | Olefins (gas) | Alcohols | | | |
| | | | | $CH_4$ | $\geq C_2$ | | | $C_1$ | $C_2$ | $>C_2$ |
| 11 | 300 | 3300 | 4.7 | 91.7 | — | — | 1.6 | 1.3 | 0.2 | 0.1 |
| 12 | 320 | 3300 | 4.5 | 65.2 | — | — | 30.4 | 30.4 | — | — |
| 13 | 340 | 3300 | 5.4 | 43.0 | — | — | 46.2 | 43.0 | 1.1 | 2.1 |
| 14 | 360 | 3300 | 5.9 | 34.0 | — | — | 58.8 | 58.3 | 0.5 | — |
| 15 | 360 | 1650 | 12.9 | 25.1 | 2.6 | — | 64.8 | 63.7 | 1.1 | — |
| 16 | 340 | 3300 | 5.9 | 24.2 | — | — | 33.4 | 32.7 | 0.7 | — |
| 17 | 360 | 3300 | 6.9 | 15.9 | — | — | 50.5 | 47.8 | 0.9 | 1.8* |
| 18 | 380 | 3300 | 12.4 | 21.2 | 4.8 | 2.5 | 15.9 | 14.6 | — | 1.3* |
| 19 | 380 | 1650 | 18.6 | 16.5 | 4.7 | 1.4 | 31.5 | 30.0 | 0.1 | 1.4* |
| 20 | 380 | 3300 | 16.3 | 16.9 | — | 7.2 | 29.1 | 25.0 | 1.0 | 3.1* |
| 21 | 380 | 1650 | 26.7 | 15.8 | 4.6 | 7.2 | 22.3 | 19.4 | — | 2.9* |
| 22 | 380 | 3300 | 4.1 | 19.7 | — | 5.5 | 10.9 | 10.2 | — | 0.7* |
| 23 | 360 | 3300 | 6.0 | 20.4 | — | 0.0 | 25.0 | 23.7 | — | 1.3* |

*Appreciable Selectivity to $>C_3$ Alcohols

Alkali metal free catalysts of the formula 10% $RuPdO_x$/90% Alundum were prepared by slurrying ruthenium oxide and palladium acetate in water, without alkali addition, heating, recovering the catalyst precursor, drying and calcining with subsequent reduction. These catalysts exhibited low selectivity to alcohols other than methanol.

EXAMPLES 7-10

Catalysts of the formula 10% $RuPdNa_{0.02-0.2}O_x$/90% Alundum were prepared according to the method first set forth above. These catalysts exhibited good selectivity to alkanes and alcohols having at least two carbon atoms.

EXAMPLES 11-25

Catalysts prepared in the following examples were tested for synthesis gas upgrading in a 20 cc reactor wherein temperature variation corresponded only to the normal exotherm or "hot spot" temperature zone generally associated with fixed-bed reactors. Reaction conditions included a $CO/H_2$ ratio of 3/7 and a reaction pressure of about 1,300 psi. Reaction temperature and

EXAMPLES 11-15

Catalysts of the formula 10% $RuPdNa_{0.02-0.2}O_x$/90% Alundum were prepared according to the method set forth in Examples 7-10. These catalysts all exhibited selective alcohol production, as demonstrated in Table IV.

EXAMPLES 16-19

Catalysts of the formula 10% $RuPdNa_{0.2}O_x$/90% Alundum were prepared according to the procedure of Examples 7-10 except that additional alkali in the form of sodium was added to the catalyst. These catalysts exhibited good selectivity to alcohol production, including alcohols having more than three carbon atoms.

EXAMPLES 20-21

Catalysts of the formula 10% $RuPdNa_{0.4}O_x$/90% Alundum were prepared according to the method of Examples 16-19, except that the sodium level was doubled. These catalysts also exhibited good selectivity to alcohols, including alcohols having more than three carbon atoms.

EXAMPLES 22-23

Catalysts of the formula 10% $RuPdRb_{0.4}O_x$/90% Alundum were prepared according to the method of Examples 20-21 except that rubidium was substituted for the sodium as the alkali metal oxide. These catalysts also exhibited good selectivity to alcohol production, including alcohols having more than three carbon atoms.

Although under certain conditions the above-identified catalysts may produce olefins and other hydrocarbons in the synthesis gas upgrading process, these catalysts are most suitable for the production of alkanes including alkanes having at least two carbon atoms and alcohols including alcohols having more than one carbon atom.

Thus it should be apparent to those skilled in the art that the subject invention accomplishes the objects set forth above. It is to be understood that the subject invention is not to be limited by the examples set forth herein. These have been provided merely to demonstrate operability and the selection of catalyst component containing compounds, catalyst formulations, synthesis gas component ratios and reaction conditions can be determined from the total specification disclosure provided without departing from the spirit of the invention herein disclosed and described. The scope of the invention includes equivalent embodiments, modifications and variations that fall within the scope of the attached claims.

We claim:

1. A catalyst for the upgrading of synthesis gas to alcohol products of the formula $$A_aRuM_bO_x$$

wherein
 A is an alkali metal
 M is Pd, Pt or mixtures thereof, and
wherein
 a is about 0.002 to about 2,
 b is about 0.1 to about 10, and
 x is the number of oxygens needed to fulfill the valence requirements of the other elements.

2. A catalyst as in claim 1 wherein A is selected from sodium, potassium and rubidium.

3. A catalyst as in claim 1 wherein a is 0.02 to 1.

4. A catalyst as in claim 1 wherein M is Pd.

5. A catalyst as in claim 1 wherein b is about 1.

6. A catalyst as in claim 1 or 4 wherein said catalyst is partially reduced.

7. A catalyst as in claim 1 or 4 wherein said catalyst is supported on an inert carrier.

8. A catalyst as in claim 7 wherein said carrier is selected from alumina, silica, alumina-silica, Alundum, clay, silicon-carbide and mixtures thereof.

* * * * *